US006794331B2

(12) United States Patent
Ostgard et al.

(10) Patent No.: US 6,794,331 B2
(45) Date of Patent: Sep. 21, 2004

(54) RANEY COPPER

(75) Inventors: Daniel Ostgard, Kleinostheim (DE); Jorg Sauer, Geinhausen (DE); Andreas Freund, White Plains, NY (US); Monika Berweiler, Maintal (DE); Matthias Hopp, Mobile, AL (US); Rudolf Vanheertum, Kahl (DE); Walther Girke, Hanau-Grossauheim (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/266,588

(22) Filed: Oct. 9, 2002

(65) Prior Publication Data

US 2003/0125200 A1 Jul. 3, 2003

Related U.S. Application Data

(63) Continuation of application No. 09/783,387, filed on Feb. 15, 2001, now abandoned.
(60) Provisional application No. 60/198,755, filed on Apr. 21, 2000.

(30) Foreign Application Priority Data

Feb. 18, 2000 (EP) .............................................. 00103546

(51) Int. Cl.⁷ ................................................. B01J 25/00
(52) U.S. Cl. ...................................... 502/301; 502/331
(58) Field of Search ................................. 502/301, 330, 502/331, 344, 345, 327

(56) References Cited

U.S. PATENT DOCUMENTS

| | | | |
|---|---|---|---|
| 3,243,171 A | * | 3/1966 | Hoffman et al. ............ 564/127 |
| 3,839,011 A | | 10/1974 | Larson, Jr. |
| 4,166,805 A | | 9/1979 | Jowett |
| 4,347,383 A | | 8/1982 | Isshiki et al. |
| 4,826,799 A | | 5/1989 | Cheng et al. |
| 4,895,994 A | | 1/1990 | Cheng et al. ................ 585/270 |
| 5,015,766 A | | 5/1991 | Kambara et al. |
| 5,292,936 A | | 3/1994 | Franczyk |
| 5,435,984 A | | 7/1995 | Daly et al. |
| 5,536,694 A | | 7/1996 | Schuetz et al. |
| 5,789,593 A | | 8/1998 | Weiguny et al. |
| 5,936,081 A | | 8/1999 | Degelmann et al. |
| 6,028,119 A | | 2/2000 | Kokubu et al. |
| 6,087,296 A | | 7/2000 | Harper |
| 6,121,188 A | | 9/2000 | Breitscheidel et al. |
| 6,153,554 A | | 11/2000 | Petro |
| 6,284,703 B1 | | 9/2001 | Ostgard et al. |

FOREIGN PATENT DOCUMENTS

| | | |
|---|---|---|
| DE | 1 401 673 | 7/1975 |
| EP | 0 175 581 | 3/1986 |
| EP | 0 321 152 | 6/1989 |
| EP | 0 651 734 | 3/1994 |
| EP | 0 620 205 | 4/1994 |
| EP | 0 734 765 | 10/1996 |
| EP | 1 127 613 | 2/2000 |
| EP | 1 067 114 | 1/2001 |
| GB | 596758 | 8/1945 |
| GB | 766677 | 5/1954 |
| GB | 817622 | 3/1957 |
| JP | 11 279 090 | 10/1999 |

OTHER PUBLICATIONS

Database WPI, Derwent Publications Ltd., London, GB; ZP002169056 and JP 50 093919 (Mitsui Toatsu Chem Inc.), Jul. 1975.
English language abstract of foreign patent document MR.

* cited by examiner

*Primary Examiner*—Stuart Hendrickson
(74) *Attorney, Agent, or Firm*—Smith, Gambrell & Russell, LLP

(57) ABSTRACT

Raney copper which is doped with at least one metal from the group comprising iron and/or noble metals is used as a catalyst in the dehydrogenation of alcohols.

2 Claims, 1 Drawing Sheet

RANEY COPPER

This is a continuation application of Ser. No. 09/783,387, filed Feb. 15, 2001, now abandoned, which claims priority to Provisional Serial No. 60/198,755, filed Apr. 21, 2000, which claims priority to European Application No. 00103546.8, filed Feb. 18, 2000.

BACKGROUND OF THE INVENTION

1. Field of the Invention

This invention relates to Raney copper, to a process for the production thereof and to a process for dehydrogenating alcohols.

2. Background Information

It is known to dehydrogenate diethanolamine to yield iminodiacetic acid (U.S. Pat. No. 5,689,000; WO 96/01146; WO 92/06949; published patent application JP 091 55 195; U.S. Pat. No. 5,292,936; U.S. Pat. No. 5,367,112; CA 212 10 20).

SUMMARY OF THE INVENTION

The present invention provides Raney copper which is characterised in that it is doped with at least one metal from the group comprising iron and/or noble metal.

Doping may be achieved both by alloying the doping element with the Raney alloy, which consists of copper and aluminium, and by impregnating the previously prepared Raney copper with the doping element.

The Raney copper according to the invention may contain the doping elements in a quantity of 10 ppm to 5 wt. %. Noble metal doping may amount to 10 to 50000 ppm, preferably 500 to 50000 ppm. The doping metals may be selected from the group comprising iron and palladium, platinum, gold, rhenium, silver, iridium, ruthenium and/or rhodium.

The Raney copper according to the invention may comprise meso- and macropores, but no micropores.

The inital formed alloy can contain more than 50% Cu so that the finished catalyst contains more residual Al than normally found under the same activation conditions.

The initial formed alloy can be heat treated in air temperatures higher than 500° C. activation.

The initial formed alloy can contain more than 50% Cu and heat treated in air temperatures higher than 500° C. before activation.

The average particle size of the Raney copper according to the invention may be 35±30 $\mu$m.

The average particle size of the Raney copper according to the invention is of significance during use in oxidation reactions or alcohol dehydrogenation reactions.

On repeated use, known Raney copper forms granules (agglomerates), so deactivating the Raney copper.

The Raney copper according to the invention doped with iron and/or noble metal is not deactivated by unwanted granulation. Advantageously, the Raney copper according to the invention may readily be filtered.

The Raney copper according to the invention exhibits greater activity in the dehydrogenation of ethylene glycol than the Cr/Raney copper according to EP 0 620 209 A1 or U.S. Pat. No. 5,292,936.

The Raney copper according to the invention furthermore advantageously contains no toxic metals, such as chromium for example.

The present invention also provides a process for the production of the Raney copper, which process is characterised in that a copper/aluminium alloy is activated by means of an aqueous sodium hydroxide solution, the catalyst is washed, suspended in water, an iron salt or noble metal salt solution is added to this suspension, the pH value of the solution is adjusted to a value from 4 to 11, the catalyst is separated from the solution and washed.

The present invention also provides a process for the production of the Raney copper, which process is characterised in that the doping metal is alloyed together with copper and aluminium, is then activated by means of aqueous sodium hydroxide solution and the catalyst is washed.

The present invention also provides a process for the catalytic dehydrogenation of alcohols to their corresponding carbonyls and carboxylic acids, which process is characterised in that a Raney copper doped with iron or noble metal is used as the catalyst.

The process according to the invention for the dehydrogenation of alcohols may be used for dehydrogenating glycols and/or aminoalcohols. The catalyst may be used in the form of a suspension for such reactions.

The alcohols which may be dehydrogenated according to the invention may be mono- or polyhydric alcohols. Said alcohols, including polyether glycols, may be aliphatic, cyclic or aromatic compounds which react with a strong base to yield the carboxylate.

It is necessary in this connection that the alcohol and the resultant carboxylate are stable in a strongly basic solution and that the alcohol is at least somewhat soluble in water.

Suitable primary, monohydric alcohols may include:

aliphatic alcohols, which may be branched, linear, cyclic or aromatic alcohols, such as for example benzyl alcohol, wherein these alcohols may be substituted with various groups which are stable in bases.

Suitable aliphatic alcohols may be ethanol, propanol, butanol, pentanol or the like.

According to the invention, glycols may be oxidised or dehydrogenated to yield carboxylic acids. Glycols may, for example, be:

ethylene glycol propylene glycol 1,3-propanediol butylene glycol 1,4-butanediol

It is thus possible, for example, to dehydrogenate ethylene is glycol to yield glycolic acid (monocarboxylic acid) and to produce the dicarboxylic acid oxalic acid by subsequent reaction with KOH.

Aminoalcohols may also be dehydrogenated with the doped Raney copper according to the invention to yield the corresponding aminocarboxylic acids. The amino alcohols may have 1 to 50 C atoms.

It is accordingly possible, for example, to dehydrogenate N-methylethanolamine to yield sarcosine; THEEDA (tetrahydroxyethylethylenediamine) to yield the tetrasodium salt of EDTA (ethylenediaminetetraacetate); monoethanolamine to yield glycine; diethanolamine to yield iminodiacetic acid; 3-amino-1-propanol to yield beta-alanine; 2-amino-1-butanol to yield 2-aminobutyric acid.

In one embodiment of the invention, the process according to the invention may be used to dehydrogenate aminoalcohols of the formula

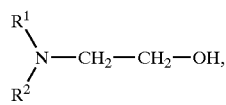

in which $R^1$ and $R^2$ each mean hydrogen; hydroxyethyl; —CH$_2$CO$_2$H; an alkyl group having 1 to 18 C atoms; an aminoalkyl group having 1 to 3 C atoms; a hydroxyalkylaminoalkyl group having 2 to 3 C atoms and phosphonomethyl.

The aminoalcohols which may be used according to the invention are known. If $R^1$ and $R^2$ are hydrogen, the aminoalcohol is diethanolamine.

If $R^1$ and $R^2$ are hydroxyethyl, the aminoalcohol is triethanolamine. The resultant aminocarboxylic acid salts of these starting aminoalcohols should be the salts of glycine, iminodiacetic acid and nitrilotriacetic acid respectively. Further aminoalcohols comprise N-methylethanolamine, N,N-dimethylethanolamine, N-ethylethanolamine, N-isopropylethanolamine, N-butylethanolamine, N-nonylethanolamine, N-(2-aminoethyl)ethanolamine, N-(3-aminopropyl)ethanolamine, N,N-diethylethanolamine, N,N-dibutylethanolamine, N-methyldiethanolamine, N-ethyldiethanolamine, N-isopropyldiethanolamine, N-butyldiethanolamine, N-ethyl-N-(2-aminoethyl)-ethanolamine, N-methyl-N-(3-aminopropyl)ethanolamine, tetra(2-hydroxyethyl)ethylenediamine and the like.

Further examples of aminocarboxylic acid salts are the salts of N-methylglycine, N,N-dimethylglycine, N-ethylglycine, N-isopropylglycine, N-butylglycine, N-nonylglycine, N-(2-aminoethyl)glycine, N-(3-aminopropyl) glycine, N,N-diethylglycine, N,N-dibutylglycine, N-methyliminodiacetic acid, N-ethyliminodiacetic acid, N-isopropyliminodiacetic acid, N-butyliminodiacetic acid, N-ethyl-N-(2-aminoethyl) glycine, N-methyl-N-(3-aminopropyl)glycine, ethylenediaminetetraacetic acid etc.

$R^1$ or $R^2$ may also be a phosphonomethyl group, wherein the starting amino compound may be N-phosphonomethylethanolamine and the resultant amino acid N-phosphonomethylglycine. If, of $R^1$ or $R^2$, one R=phosphonomethyl and the other R=—CH$_2$CH$_2$OH, the resultant amino acid would be N-phosphonomethyliminodiacetic acid, which may be converted in known manner into N-phosphonomethylglycine. If, of $R^1$ or $R^2$, one R=phosphonomethyl and the other R is an alkyl group, the resultant acid would be N-alkyl-N-phosphonomethylglycine, which may be converted into N-phosphonomethylglycine in accordance with U.S. Pat. No. 5,068,404.

The process according to the invention may be performed at is a temperature of 50 to 250° C., preferably of 80 to 200° C., and at a pressure of 0.1 to 200 bar, preferably at standard pressure to 50 bar.

The pressure is required because the alcohols have an elevated vapour pressure. If the pressure were too low, the alcohol would also be discharged when the hydrogen was discharged.

DETAILED DESCRIPTION OF THE INVENTION

Example 1

Production of the Catalyst According to the Invention

An alloy consisting of 50% Cu/50% Al is activated with an aqueous sodium hydroxide solution. The corresponding catalyst is washed until the sodium aluminate has been completely removed. Hexachloroplatinum is then added to the suspension of the washed catalyst. The pH value is adjusted and stirring of the suspension is continued. The doped catalyst is then washed. The platinum content of the catalyst is 1%. The activity of this catalyst for dehydrogenating ethylene glycol is 299 ml of hydrogen per hour per gram of catalyst (c.f. Example 3).

Example 2

Production of the Catalyst According to the Invention

An alloy consisting of 50% Cu/50% Al is activated with an aqueous sodium hydroxide solution. The corresponding catalyst is washed until the sodium aluminate has been completely removed. Iron (III) chloride is then added to the suspension of the washed catalyst. The pH value is adjusted and stirring of the suspension is continued. The doped catalyst is then washed. The iron content of the catalyst is 3%.

Example 3

Dehydrogenation of ethylene glycol to yield sodium glycolate and sodium oxalate by means of the activated catalyst according to the Example is performed at 108° C. and atmospheric pressure. 70 ml of ethylene glycol are first added to a heterogeneous suspension of 8 grams of catalyst and 70 ml of an aqueous sodium hydroxide solution. The suspension is stirred at 400 rpm. The rate of reaction is measured by means of the quantity of hydrogen evolved between 30 and 90 minutes from the beginning of the reaction. The results are stated as ml of hydrogen per hour per gram of catalyst. The activity of this catalyst for dehydrogenating ethylene glycol is 299 ml of hydrogen per hour per gram of catalyst.

Example 4

Comparative Example

An alloy consisting of 50% Cu/50% Al is activated with an aqueous sodium hydroxide solution. The corresponding catalyst is washed until the sodium aluminate has been completely removed. The activity of this catalyst for dehydrogenating ethylene glycol is 205 ml of hydrogen per hour per gram of catalyst.

Example 5

Comparative Example

A 50% Cu/50% Al alloy is activated with an aqueous sodium hydroxide solution. The corresponding catalyst is washed until the sodium aluminate has been completely removed. Chromium nitrate is added to the suspension of the washed catalyst, the pH value adjusted, stirring of the suspension is continued and the doped catalyst washed once more. The chromium content in the catalyst is 2000 ppm. The activity of this catalyst for dehydrogenating ethylene glycol is 253 ml of hydrogen per hour per gram of catalyst.

Example 6

Comparative Example

A Cu/Al/V alloy is activated with an aqueous sodium hydroxide solution. The corresponding catalyst is washed until the sodium aluminate has been completely removed. The content of V in the catalyst is 1%. The activity of the catalyst for dehydrogenating ethylene glycol is 253 ml of hydrogen per hour per gram of catalyst.

Example 7

Production of Iminodiacetic Acid with Platinum on Raney Copper as Catalyst

The Example illustrates the conversion of diethanolamine (DEA) to yield the sodium salt of iminodiacetic acid (IDA) with Pt-doped Raney copper as catalyst.

The tests are performed in a 2 L Büchi autoclave. The autoclave is equipped with a sparging agitator, which is operated at a standard speed of 500 min-l (sic). The autoclave is equipped with a jacket. The temperature in the autoclave may be adjusted by means of a temperature controlled oil bath.

The following materials are initially introduced into the autoclave:

318.8 g of diethanolamine (3 mol)
508 g of aqueous NaOH solution (50 wt. %, 6.3 mol NaOH)
64 g of catalyst according to the invention: 1% Pt on Raney copper stored under water
370 g of $H_2O$, ultrasonically degassed The autoclave is pressurised to 10 bar with nitrogen and adjusted to the reaction temperature (TR=160° C.). Once the reaction has begun, the evolved hydrogen is discharged, with the released quantity being determined by means of a dry gas meter. The reaction is terminated after a period of 5 h and the autoclave cooled. The reaction products are flushed from the autoclave with degassed water, the catalyst filtered out and the dehydrogenation products analysed by ion chromatography.

As table 1 shows, the catalyst used may be recycled repeatedly without appreciable loss of activity.

TABLE 1

Conversion of diethanolamine on Pt-doped Raney copper

| Number of batches with catalyst | IDA yield [mol %] |
| --- | --- |
| 1 | 94.3 |
| 2 | 92.5 |
| 3 | 98.6 |
| 4 | 96.8 |
| 5 | 95.0 |
| 6 | 94.7 |
| 7 | 90.9 |
| 8 | 91.8 |
| 9 | 93.4 |
| 10 | 95.8 |
| 11 | 97.7 |
| 12 | 93.5 |
| 13 | 95.7 |
| 14 | 92.6 |
| 15 | 90.0 |
| 16 | n.d. |
| 17 | n.d. |
| 18 | 95.2 |

[n.d. = not determined]

Example 6

Production of Iminodiacetic Acid with Iron on Raney Copper as Catalyst

The following materials are initially introduced into a 2 L autoclave:

318.8 g of diethanolamine (3 mol)
508 g of aqueous NaOH solution (50 wt. %, 6.3 mol NaOH)
64 g of catalyst according to the invention: 3% Fe on Raney copper stored under water
370 g of $H_2O$, ultrasonically degassed The test is performed in a similar manner to Example 5. The yields listed in Table 2 are achieved; no deactivation of the catalyst is observable even after repeated use of the catalyst.

TABLE 2

Conversion of diethanolamine on Fe-doped Raney copper

| Number of batches with catalyst | IDA yield [mol %] |
| --- | --- |
| 1 | 95.3 |
| 2 | 99.1 |
| 3 | 99.0 |
| 4 | n.d. |
| 5 | n.d. |
| 6 | 91.9 |
| 7 | n.d. |
| 8 | n.d. |
| 9 | n.d. |
| 10 | 93.7 |
| 11 | n.d. |
| 12 | n.d. |
| 13 | n.d. |
| 14 | 94.0 |

Example 7

Comparative Example

Production of Iminodiacetic Acid on Undoped Raney Copper

Pure Raney copper (Degussa catalyst BFX 3113W) is used under the conditions of Example 5. The Raney copper exhibits distinct deactivation after only a few batches. (Table 3)

TABLE 3

Conversion of diethanolamine on Raney copper

| Number of batches with catalyst | IDA yield [mol %] |
|---|---|
| 1 | 91.6 |
| 2 | 82.8 |
| 3 | 68.3 |
| 4 | 51.3 |

Example 8

Production of Glycine with Platinum on Raney Copper as Catalyst

The following materials are initially introduced into the 2 L autoclave:

307 g of monoethanolamine (5 mol)
420 g of aqueous NaOH solution (50 wt. %, 5.25 mol NaOH)
64 g of catalyst according to the invention: 1% Pt on Raney copper stored under water
400 g of $H_2O$; ultrasonically degassed The test is performed in a similar manner to Example 5. The yields listed in table 4 are achieved. No deactivation of the catalyst is observable even after repeated use of the catalyst.

TABLE 4

Conversion of monoethanolamine on Pt-doped Raney copper

| Number of batches with catalyst | Glycine yield [mol %] |
|---|---|
| 1 | 98.5 |
| 2 | 97.5 |
| 3 | n.d. |
| 4 | n.d. |
| 5 | 98.1 |

Example 9

Production of β-alanine with Platinum on Raney Copper as Catalyst

The following materials are initially introduced into the 2 L autoclave:

380 g of 3-amino-1-propanol (5 mol)
422 g of aqueous NaOH solution (50 wt. %, 5.25 mol NaOH)
64 g of catalyst according to the invention: 1% Pt on Raney copper stored under water
250 g of $H_2O$; ultrasonically degassed The test performed in a similar manner to Example 5. The yields listed in Table 5 are achieved. No deactivation of the catalyst is observable even after repeated use of the catalyst.

TABLE 5

Conversion of 3-amino-1-propanol on Pt-doped Raney copper

| Number of batches with catalyst | β-Alanine yield [mol %] |
|---|---|
| 1 | 98.2 |
| 2 | 98.3 |
| 3 | n.d. |
| 4 | n.d. |
| 5 | 98.3 |

Example 10

Production of 2-aminobutyric Acid with Platinum on Raney Copper as Catalyst The following materials are initially introduced into the 2 L autoclave:

460 g of 2-amino-1-butanol (5 mol)
392 g of aqueous NaOH solution (50 wt. %, 5.25 mol NaOH)
64 g of catalyst according to the invention: 1% Pt on Raney copper stored under water
140 g of $H_2O$; ultrasonically degassed The test is performed in a similar manner to Example 5. The yields listed in Table 6 are achieved. No deactivation of the catalyst is observable even after repeated use of the catalyst.

TABLE 6

Conversion of 2-amino-1-butanol on Pt-doped Raney copper

| Number of batches with catalyst | 2-Amino-1-butyric acid yield [mol %] |
|---|---|
| 1 | 99.2 |
| 2 | 98.1 |
| 3 | n.d. |
| 4 | n.d. |
| 5 | 98.9 |

Figure 1:
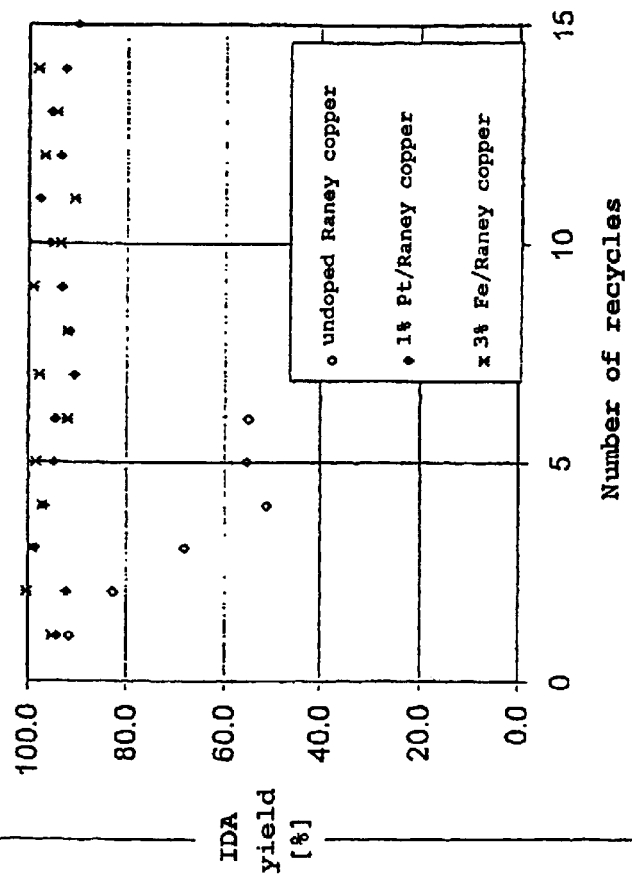
FIG. 1 shows the advantage of the catalyst according to the invention illustrated by the example of the dehydrogenation or conversion of diethanolamine to yield iminodiacetic acid.

The catalyst according to the invention exhibits a distinctly longer service life than the undoped Raney catalyst.

What is claimed is:

1. A process for the production of a Raney copper catalyst with an average particle size of from 5 μm to 65 μm, which is doped with at least one metal selected from the group consisting of iron and/or noble metals, wherein a copper/aluminum alloy is activated with an aqueous sodium hydroxide solution, the catalyst is washed, suspended in water, an iron salt or noble metal salt solution is added to the suspension, the pH is adjusted to a value of from 4 to 11, and the catalyst is separated from the solution and washed.

2. A process for the production of the Raney-copper catalyst according to claim 1, wherein the doping elements are Re, Pd, Pt, Ag, Au, Rh, Ir, Ru, Fe, and/or mixtures thereof.

* * * * *